United States Patent [19]

Voith

[11] Patent Number: 4,468,391

[45] Date of Patent: Aug. 28, 1984

[54] COMBINATION OF β-ADRENOCEPTOR ANTAGONISTS AND ANXIOLYTIC AGENTS

[75] Inventor: Katherine Voith, Dorval, Canada

[73] Assignee: Ayerst, McKenna & Harrison, Inc., Montreal, Canada

[21] Appl. No.: 392,417

[22] Filed: Jun. 25, 1982

[51] Int. Cl.³ .............................................. A61K 31/33
[52] U.S. Cl. .................................................... 424/244
[58] Field of Search ........................................ 424/244

[56] References Cited

U.S. PATENT DOCUMENTS 3,959,486  5/1976  LeCount et al. ............... 424/324
4,059,622  11/1977  LeCount et al. ............... 424/325
4,190,654  2/1980  Gherardi et al. ............... 424/244

FOREIGN PATENT DOCUMENTS 763000  8/1971  Belgium .
860526  5/1978  Belgium .
1305644  2/1973  United Kingdom .
1315450  5/1973  United Kingdom .
2052982A  2/1981  United Kingdom .

OTHER PUBLICATIONS

Z. Rolinski and W. Kozak, Pol. J. Pharmacol. Pharm., 32, 731, (1980).
C. Hallstrom et al., Brit. J. Psychiat., 139, 417, (1981).

Primary Examiner—Stanley J. Friedman
Attorney, Agent, or Firm—Arthur E. Wilfond

[57] ABSTRACT

A β-adrenoceptor antagonist, which does not penetrate or penetrates poorly the brain, is combined with subtherapeutic doses of an anxiolytic agent, such as diazepam, to give a method, and pharmaceutical or veterinary composition, for treating anxiety, stress or aggressivity without deleterious side effects associated with the central nervous system.

8 Claims, 9 Drawing Figures

FIG. 2

ISOLATION-INDUCED FIGHTING BEHAVIOR IN MICE

FIG. 9
EFFECT OF l-PROPRANOLOL ON DIAZEPAM -INDUCED MUSCLE RELAXATION

COMBINATION OF β-ADRENOCEPTOR ANTAGONISTS AND ANXIOLYTIC AGENTS

BACKGROUND OF THE INVENTION

This invention concerns a method for treating pathological states of anxiety, stress and aggressivity, and to a pharmaceutical or veterinary composition therefor. The active principle for the method and composition is an improved combination of a β-adrenoceptor (β-AA) with an anxiolytic agent, which provides an enhanced therapeutic effect without enhancing side effects.

Side effects, associated with the central nervous system (CNS), are often encountered by patients receiving one of the presently available anxiolytic agents such as diazepam and meprobamate. Sedation and impairment of motoricity are among the most serious side effects of this type. Consequently, these drugs must be used with caution by patients having activities requiring close attention or by operators of complex machinery.

I have found that by combining an anxiolytic agent with a β-AA which does not penetrate or penetrates poorly the central nervous system, it is possible to provide a treatment for anxiety which is more complete than that which would be expected by the mere addition of effects and, simultaneously and unexpectedly, avoids the above noted side effects of the presently available regimens.

Combinations of β-AA's and anxiolytic agents are known; for instance, Z. Rolinski and W. Kozak, Pol. J. Pharmacol. Pharm., 32, 731 (1980) reports that β-AA's potentiate the antiaggressive action of benzodiazepine derivatives in the foot-shock induced fighting mice. The report makes no mention of any other effects.

C. Hallstrom et al., Brit. J. Psychiat., 139, 417 (1981) studied the therapeutic benefit of combining the β-adrenoceptor antagonist propranolol with the well known anxiolytic agent diazepam in chronically anxious patients. They found that the combination was generally more effective than diazepam alone; however, they concluded that the addition of propranolol did not reduce the amount of diazepam required.

Combinations of β-AA's and anxiolytic agents also have been reported in the patent literature. For example, P. Gherardi and G. Ferrari, U.S. Pat. No. 4,190,654, Feb. 26, 1980, describe a combination of moprolol and certain benzodiazapines. H. Buhlmann and D. Welzel, U.K. patent application No. 2,052,982-A, Feb. 4, 1981, describe a composition of an indole β-AA, such as pindolol, and a benzodiazepine, such as cloxazolam, having enhanced anxiolytic activity. Belgian Pat. No. 860,526, May 8, 1978, discloses a combined formulation of either oxprenolol or metroprolol and a benzodiazepine derivative for treating anxiety. Belgian Pat. No. 763,000, Aug. 16, 1971 discloses combinations of a variety of β-AA's, including oxprenolol and practolol, with a host of different tranquilizers including neuroleptic agents, benzodiazapine derivatives and meprobamate derivatives. U.K. Pat. No. 1,315,450, published May 2, 1973, corresponds in part to Belgian Pat. No. 763,000 and discloses a combined formulation of a more limited variety of B-AA's with only certain neuroleptic agents. Furthermore, U.K. Patent Specification No. 1,305,644, Feb. 7, 1973, describes a combination of β-AA's and anxiolytic agents for the treatment of various heart diseases.

Also, D. J. LeCount and C. J. Squire, U.S. Pat. No. 3,959,486, May 25, 1976 and U.S. Pat. No. 4,059,622, Nov. 22, 1977, disclose a combination of a certain class of β-AA's with a wide variety of drugs. The combination is stated to be useful for treating heart diseases and would cover combinations of cetamolol with benzodiazepine derivatives. However, the disclosure makes no mention of the combination being useful for treating anxiety, of employing lower than usual doses of the anxiolytic agent, or of providing an anxiolytic regimen free of deleterious CNS side effects.

The combination of the present invention is distinguished from the above reported combinations in that it combines a less than usual therapeutic dose of an anxiolytic agent and particular β-AA's to provide an anxiolytic regimen free of deleterious CNS side effects.

SUMMARY OF THE INVENTION

A method is provided for treating pathological states of anxiety, stress or aggressivity in a mammal, without eliciting sedative effects or impairing motoricity, which comprises administering to the mammal an effective amount of a combination of a β-AA, which does not penetrate or penetrates poorly the brain, with one quarter to one half of the normally effective dose of an anxiolytic agent. Examples of suitable β-AA's are those selected from the group consisting of cetamolol, atenolol, nifenalol, sotalol, acebutalol, nadolol, carteolol and timolol. A pharmaceutical or veterinary composition for treating states of anxiety, stress or aggressivity, without eliciting sedative effects or impairing motoricity, also is provided. The composition comprises in unit dosage form a β-AA, which does not penetrate or penetrates poorly the brain; a subtherapeutic amount of an anxiolytic agent; and a pharmaceutically acceptable carrier. Again, examples of suitable β-AA's are those selected from the group consisting of cetamolol, atenolol, nifenaolo, sotalol, acebutalol, nadolol, carteolol and timolol.

DETAILS OF THE INVENTION

The term "anxiolytic agent" as used herein means those therapeutic agents used for the management of anxiety disorders or for the short-term relief of the symptoms of anxiety. The two most widely used classes are the propanediol carbonates (e.g. meprobamate and congeners) and the benzodiazepines (e.g. diazepam and congeners). Also included within this category are the non-benzodiazepine anxiolytic agents. The latter agents are characterized by having a non-benzodiazepine chemical structure but are able to exert the anxiolytic effects of the benzodiazepine anxiolytic agents. Examples of such agents are fenobam, cartazolate, buspirone and tracazolate.

The following table lists examples of suitable anxiolytic agents for the present combination together with their normal daily dosages as reported in the literature.

| | Recommended daily human dose range, po | |
|---|---|---|
| Anxiolytic Agent | mg/patient | mg/kg |
| meprobamate | 1200–1600 | 17–23 |
| diazepam | 8–40 | 0.11–0.6 |
| temazepam | 15–30 | 0.22–0.42 |
| chlorazepate dipotassium | 15–60 | 0.22–0.84 |
| flurazepam hydrochloride | 15–30 | 0.22–0.42 |
| lorazepam | 2–6 | 0.03–0.09 |
| prazepam | 20–60 | 0.29–0.84 |
| triazolam | 0.25–0.5 | 0.036–0.072 |

-continued

| Anxiolytic Agent | Recommended daily human dose range, po | |
|---|---|---|
| | mg/patient | mg/kg |
| halazepam | 60–160 | 0.84–2.3 |
| oxazepam | 30–120 | 0.42–1.68 |
| alprazolam | 0.25–4 | 0.036–0.06 |
| chlordiazepoxide hydrochloride | 25–100 | 0.36–1.4 |
| clonazepam | 15–20 | 0.22–0.29 |

A variety of reviews describing anxiolytic agents are available. Recent comprehensive reviews of these classes of drugs are found, for example, in "Psychotherapeutic Drugs", Part 11, E. Usdin and I. S. Forrest, Eds., Marcel Dekker, Inc., New York and Basel, 1977 pp. 699–1130, and "The Pharmacological Basis of Therapeutics", L. S. Goodman and A. Gilman, Eds., 5th ed., Collier-Macmillan Canada Ltd., Toronto, Canada 1978, pp 187–193.

The term "$\beta$-adrenoceptor antagonist" ($\beta$-AA) as used herein means those therapeutic agents capable of selectively blocking $\beta$-adrenergic receptors. This action decreases inotropic, chronotropic and metabolic effects on the heart. The agents are used for the treatment of hypertension, angina pectoris and cardiac arrhythmias. The particular $\beta$-AA's suited for the combination of this invention are those which do not penetrate, or penetrates poorly the central nervous system. Such $\beta$-AA's include cetamolol, atenolol, nifenalol, sotalol, acebutalol, nadolol, carteolol and timolol. Preferred $\beta$-AA's are cetamolol, atenolol, nifenalol, sotalol and timolol. Cetamolol is most preferred.

A variety of reviews describing $\beta$-AA's also are available. Recent reviews are found, for example, in "Progress in Drug Research", E. Jucker, Ed., Birkhäuser Verlog, Basel and Stuttgart, Vol. 15, 1971, pp. 104–122, and Vol. 25, 1981, pp. 55–67; and Berger's Medicinal Chemistry, M. E. Wolff, Ed, 4th ed., John Wiley & Sons, New York, N.Y., U.S.A., 1981, pp. 310–313.

The following table lists examples of suitable $\beta$-AA's for the present combination together with daily dosages for treating hypertension as reported in the literature.

| $\beta$-AA | Recommended daily human dose range, po | |
|---|---|---|
| | mg/patient | mg/kg |
| cetamolol hydrochloride | 10–75 | 0.14–1.1 |
| atenolol | 50–100 | 0.72–1.4 |
| nifenalol | 140–700 | 2.0–10.0 |
| sotalol hydrochloride | 160–320 | 2.3–4.6 |
| acebutalol | 400–1200 | 6.0–17.0 |
| nadolol | 80–320 | 1.1–4.6 |
| carteolol | 5–25 | 0.07–0.36 |
| timolol maleate | 40–80 | 0.6–1.1 |

In practising the present invention, the anxiolytic agents and $\beta$-AA's, which have a basic nitrogen atom, can be employed in the form of the acid addition salt with a therapeutically acceptable salt. Likewise, if applicable, addition salts with organic or inorganic base of compounds having a carboxylic acid can be employed; for example clorazepate dipotassium. Hence, these addition salts are included within the scope of the invention and are limited only by the requirement that the acid, or bases, employed in forming the salt be therapeutically acceptable.

The effectiveness of the combination of this invention for treating anxiety can be demonstrated in an animal model which mimics the human condition. Namely, repeated fighting of male mice provides a natural form of intermittent periods of stress; other components of the behavior are psychological.

For example, an accurate test for anxiolytic properties involves the pharmacological control of aggressive behavior in mice according to the method described by L. Valzelli et al., Eur. J. Pharmacol., 2, 144 (1967).

More explicitly, albino mice (14–16 g) were isolated for six weeks. The isolation induced an aggressive behavior, manifested as fierce fighting, whenever two isolated mice were placed in the same cage for a period of five minutes. Only those mice which exhibited maximal fighting were kept for drug evaluation. The mice were treated only a week or after longer time intervals. To ascertain that the mice maintained their aggressiveness, their behavior in response to distilled water was periodically evaluated.

The animals were observed in the morning during a two minute control session to ascertain if maximal fighting occurred in both members of the pair. The number of fighting episodes was counted during a five minute test session conducted 30 or 60 min after the injection of graded doses of an anxiolytic agent (for example, diazepam) or a $\beta$-adrenoceptor antagonist, respectively. In separate experiments graded doses of one of the $\beta$-adrenoceptor blockers were combined with a subthreshold dose of the anxiolytic agent, for example, diazepam (0.25 mg/kg i.p.). The aforementioned time schedules were used.

The results were expressed as (a) the mean ($\pm$S.E.M.) number of fighting episodes in vehicle- and drug-treated groups, the comparison being made by Student's t-test, and (b) dose-response curves. The parallelism of the dose-response curves was determined by analysis of variance and the potency of the combined treatment determined versus the treatment with the $\beta$-adrenoceptor antagonist alone, D. J. Finney in "Statistical method in biological assay", MacMillan Publishing Co., New York, N.Y., U.S.A., 1978, pp. 39–68 and 69–104.

The results obtained by testing diazepam in the preceding test are summarized in the following table.

| Treatment | mg/kg | No. pairs | % Change vs vehicle |
|---|---|---|---|
| vehicle | | 5 | |
| diazepam | 0.75 | 5 | −48 |
| | 0.50 | 5 | −17 |
| | 0.25 | 5 | +0.9 |

The invention now will further be described with reference to the drawing, wherein.

Figure 1:
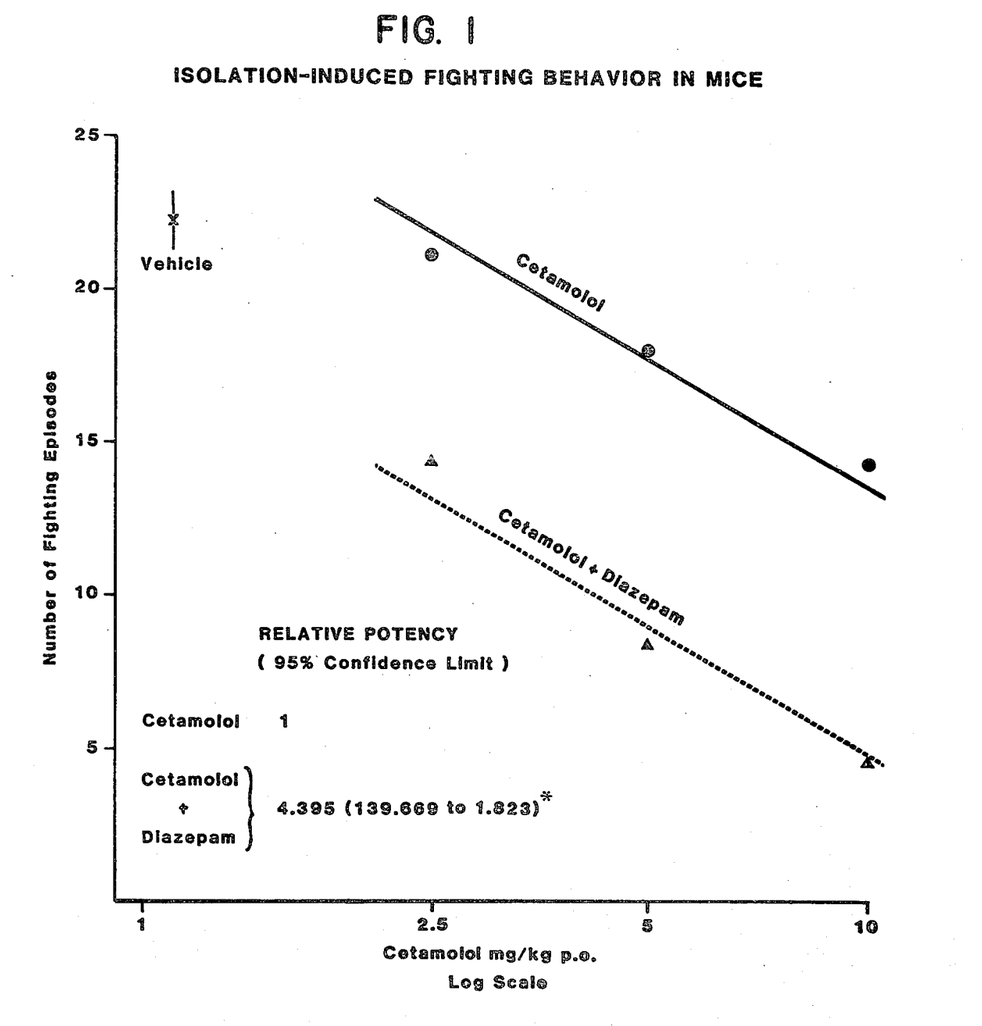
FIGS. 1 and 2 show that the combinations of certain $\beta$-AA's and anxiolytic agents are several times more potent than the $\beta$-AA alone in calming fighting behavior in mice.
Figure 2:
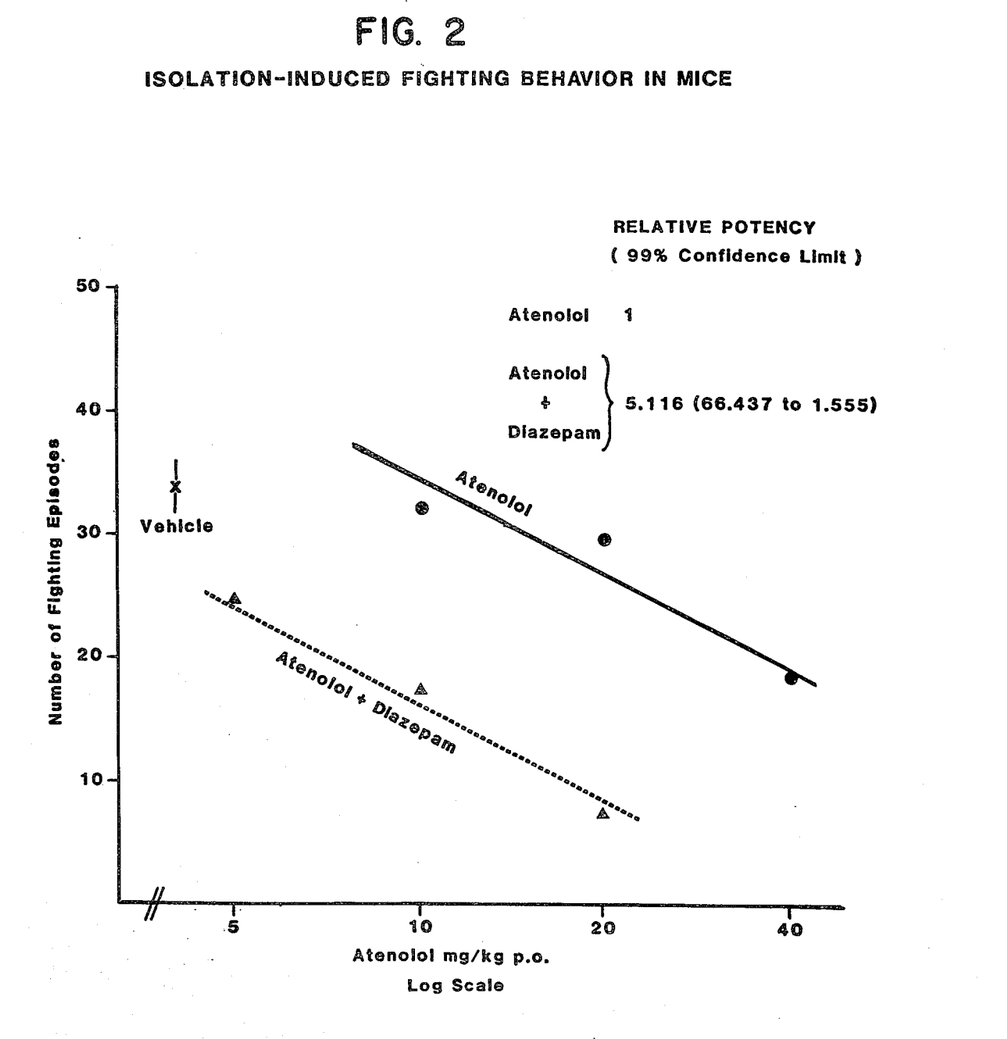

Returning to the table and FIGS. 1 and 2, the data illustrated therein show that (a) diazepam (0.25-0.75 mg/kg, i.p.), cetamolol (2.5-10 mg/kg, p.o.) and atenolol (10-40 mg/kg, p.o.) attenuate fighting behavior in mice in a dose dependent fashion; and (b) both cetamolol and atenolol potentiate diazepam.

With further reference to FIGS. 1 and 2, a detailed analysis of the above study on the attenuation of isolation-induced fighting behavior established that the dose-response curves for cetamolol and "diazepam+cetamolol" were parallel and that the combined treatment was 4.4 times more potent ($P<0.05$) than cetamolol alone (see FIG. 1), and that the dose-response curves for atenolol and "diazepam+atenolol" were parallel and that the combined treatment was 5.1 times more potent ($P<0.05$) that atenolol alone (see FIG. 2).

The feature that the combination of the present invention does not elicit central nervous system effects, for instance, sedative properties or deleterious effects on muscle coordination, also can be demonstrated in pharmacologic tests.

Figure 3:
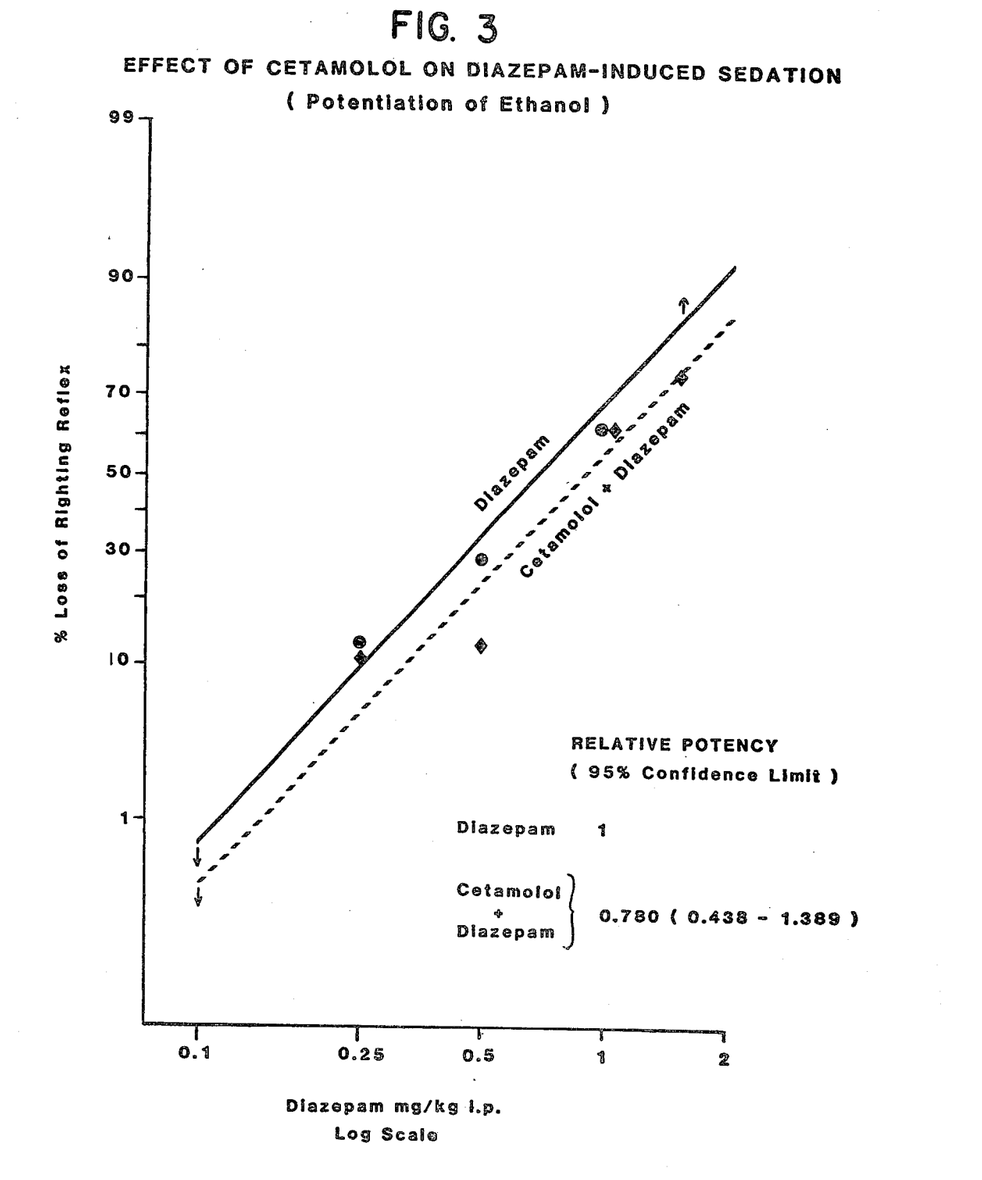
FIGS. 3 and 4 show the lack of effect the $\beta$-AA's on anxiolytic agent induced sedation.
Figure 4:
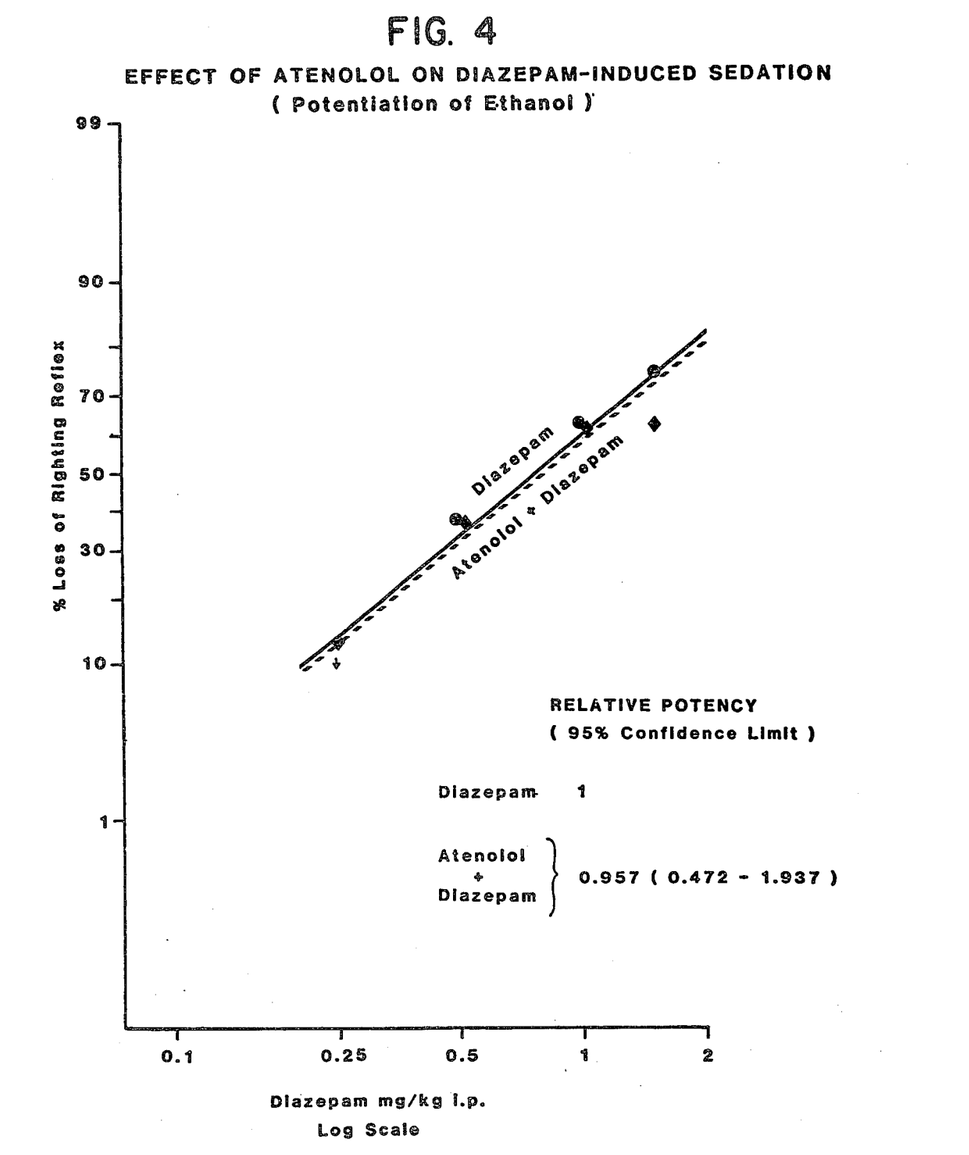

For instance, when cetamolol (10 mg/kg, po) in combination with diazepam (ranging from 0.1 to 1.5 mg/kg, ip), and atenolol (40 mg/kg, po) in combination with diazepam (ranging from 0.25 to 1.5 mg/kg, ip), were investigated in the potentiation of ethanol test in mice, as described by A. D. Rudzik et al., in "The Benzodiazepines", S. Garattini et al., Eds., Raven Press, New York, N.Y., U.S.A., 1973, p. 285, neither cetamolol nor atenolol potentiated diazepam-induced sedation (see FIGS. 3 and 4).

Figure 5:
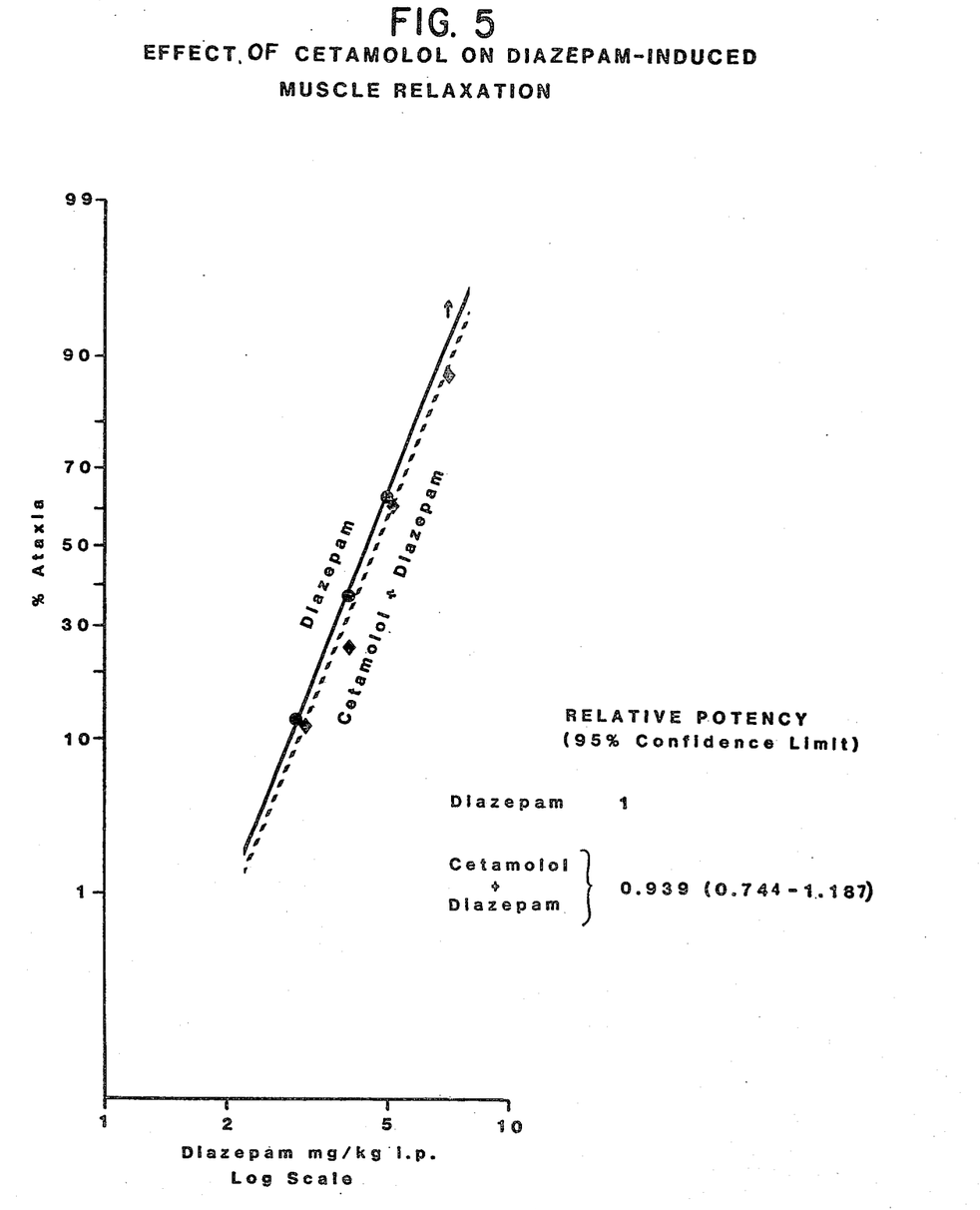
FIGS. 5 and 6 show the lack of effect of the $\beta$-AA's on anxiolytic agent induced muscle relaxation.
Figure 6:
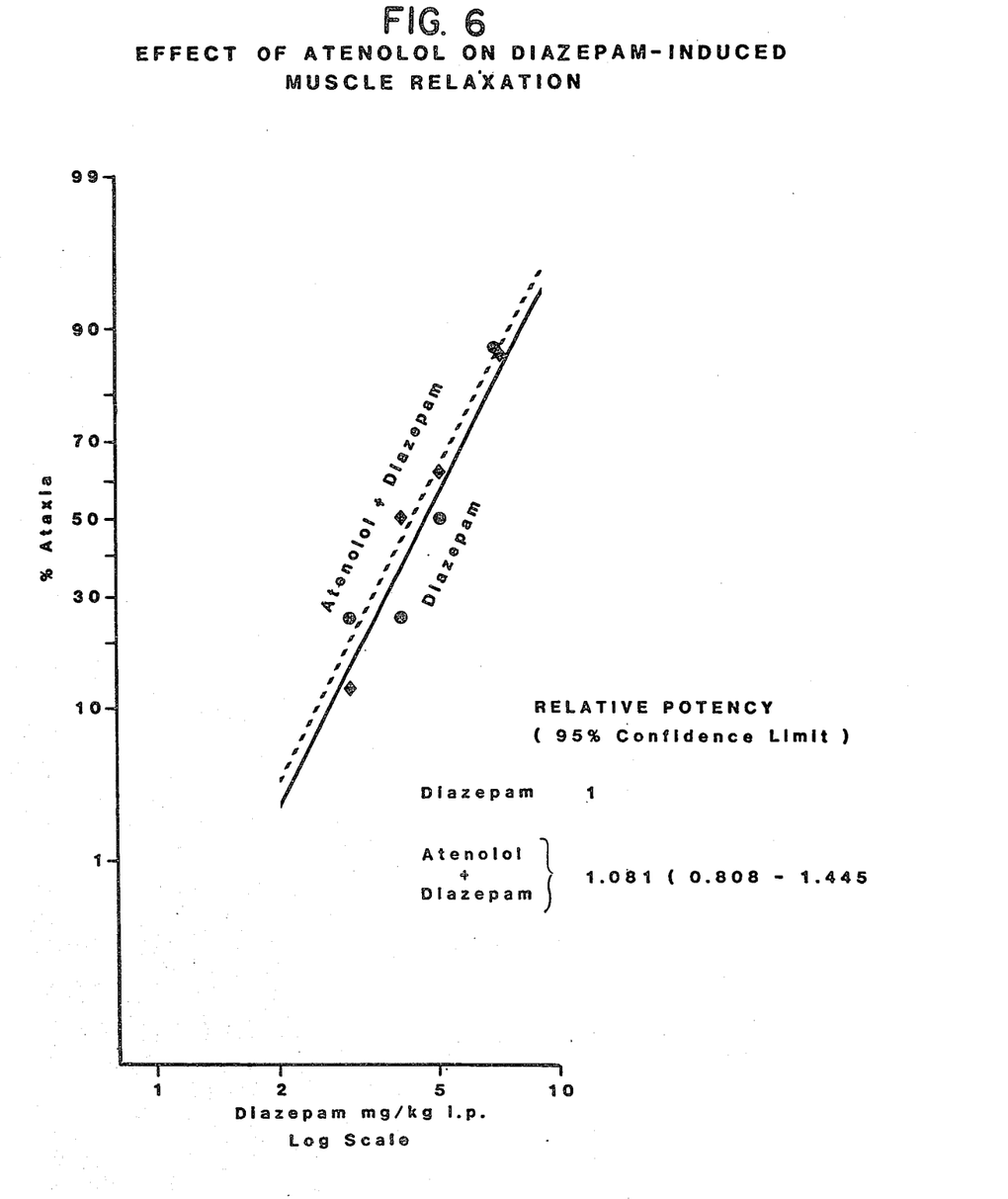

Furthermore, when combinations of cetamolol (10 mg/kg, po) and diazepam (3.0 to 7.0 mg/kg, ip), and combinations of atenolol (40 mg/kg, po) and diazepam (3.0 to 7.0 mg/kg, ip), were evaluated for their action on the muscle relaxant effect of diazepam in mice, according to the method of N. W. Dunham and T. S. Miya, J. Amer. Pharm. Ass., 46, 208 (1957), neither combination caused a change or potentiation of the latter effect (see FIGS. 5 and 6).

Figure 7:
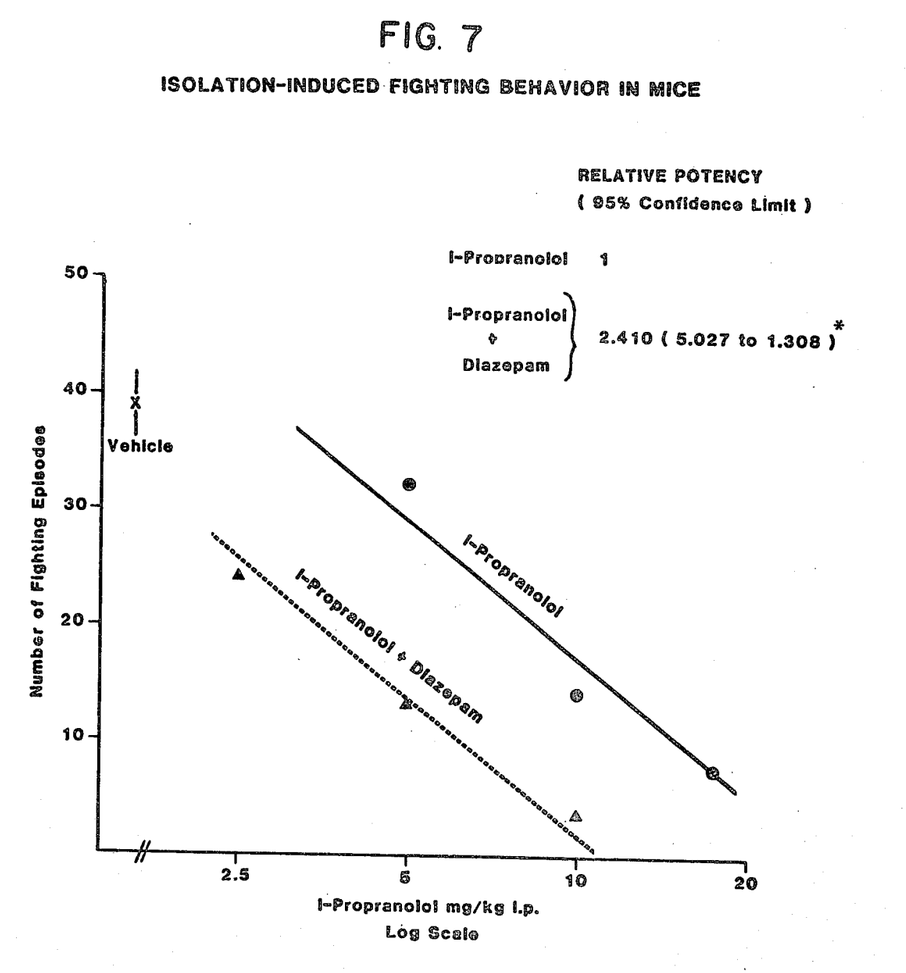
FIG. 7 shows that the combination of 1-propanolol and diazepam is only twice as effective as 1-propranolol alone.
Figure 8:
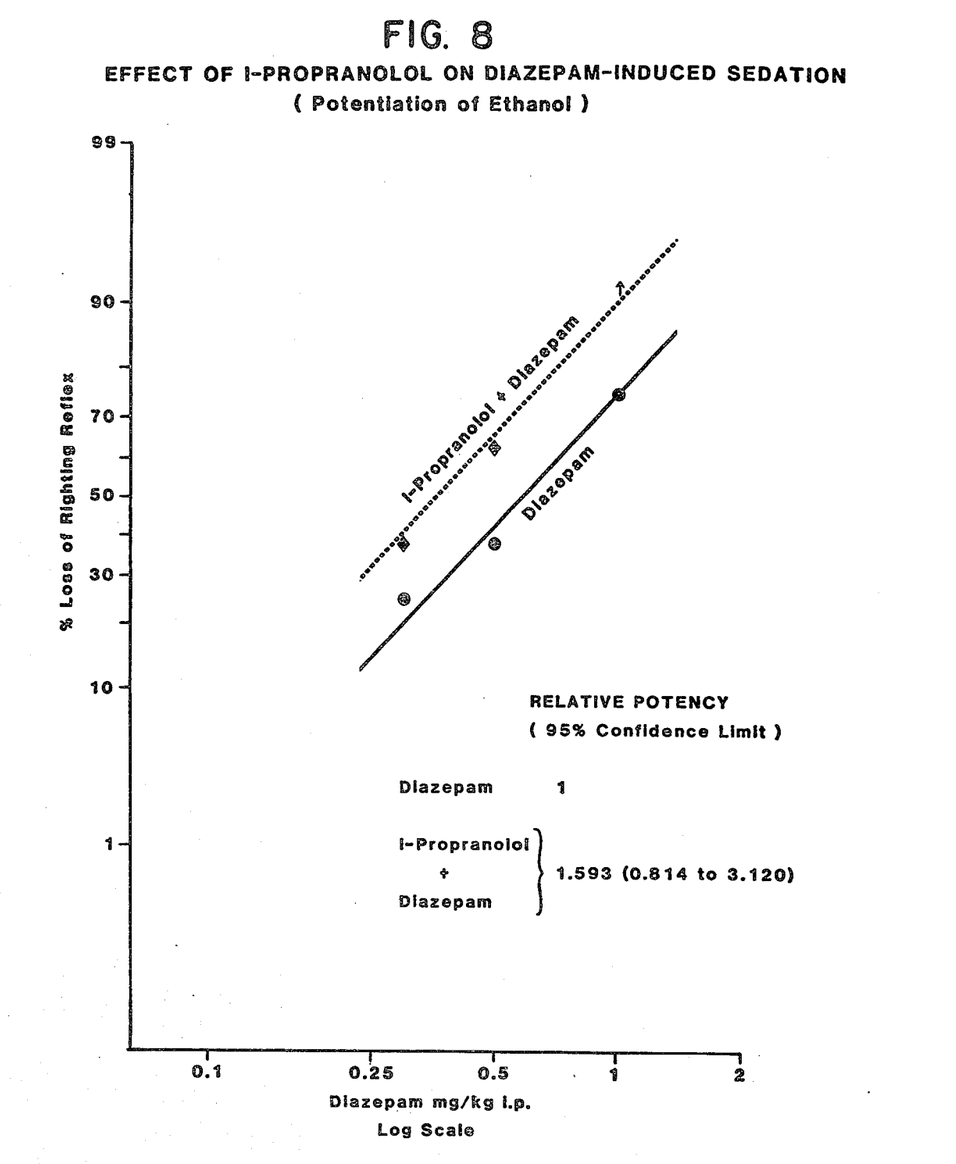
FIGS. 8 and 9 show that on the other hand 1-propranolol also potentiates diazepam induce sedation and muscle relaxation, respectively.
Figure 9:
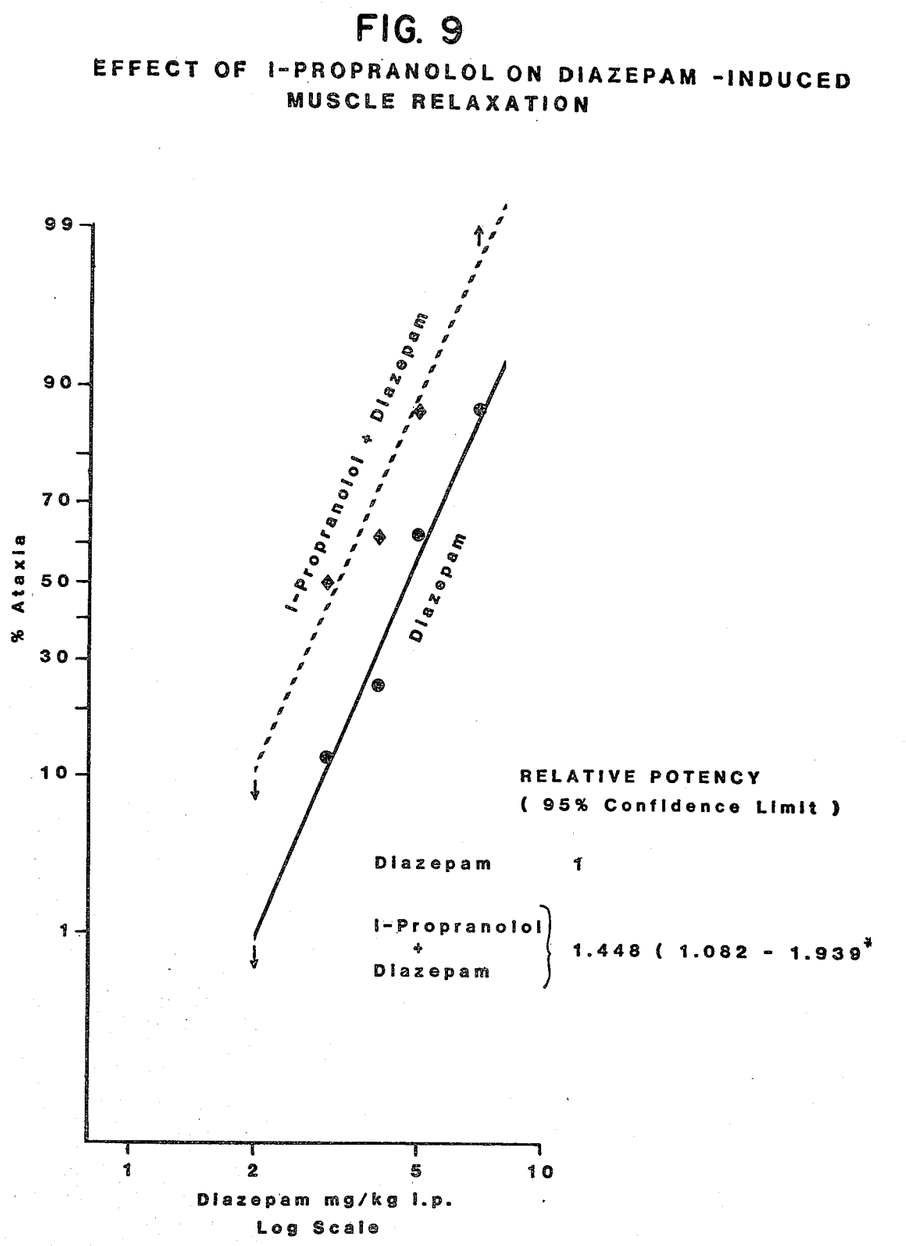

On the other hand, 1-propranolol, a β-AA which enters the brain, potentiates the therapeutic effect of diazepam (see FIG. 7) as well as the undesirable CNS side effects such as sedation and impairment of muscle copordination (see FIGS. 8 and 9).

Accordingly, the preceding pharmacological tests demonstrate that a high order of the calming effect of diazepam can be obtained in mice pretreated with cetamolol or atenolol, without sedation or loss of muscle control.

The therapeutic treatment of this invention comprises the administration of the two agents, i.e. and anxiolytic agent and a β-AA, to a mammalian subject, e.g. man, cattle or dog, in need of treatment for anxiety. The two active agents can be administered separately, or in combination, as long as the necessary daily doses are administered. Generally, treatment is initiated with small dosages substantially less than the optimum dose of the combination. Thereafter, the dosage is increased by small increments until the optimum effect under the circumstances is reached. In general, the combination of this invention is most desirably administered at a concentration level that will generally afford effective results without causing any harmful or deleterious side effects and preferably at a level which employs about one quarter to one half of the normal effective dose of the anxiolytic agent together with the usual therapeutic dose of the β-AA. For example, suitable peroral doses of diazepam are between 0.03 to 0.28 mg/kg of body weight per day, when the diazepam is given concurrently with a therapeutic dose of the β-AA. Thus, in this instance, the aforementioned dosage of diazepam is given with daily peroral doses of 0.14 to 1.1 mg/kg of body weight per day of cetamolol, or with a daily peroral dose of 0.72 to 1.4 mg/kg of body weight per day of atenolol.

The method of this ivention can be practiced using available formulations of the β-AA's for hypertension and suitable low dosage formulations of the anxiolytic agents which can be prepared readily by methods known in the art.

However, a convenient and practical adjunct to the practice of the method is a pharmaceutical or veterinary composition comprising the combination of the β-AA and a subtherapeutic amount of the anxiolytic agent admixed with a pharmaceutically acceptable carrier in a unit dosage form. The term "subtherapeutic amount" means an amount less than that which normally would produce an anxiolytic effect when given to a mammal; the amount usually is one quarter to one half the normal daily dosage. When the amount is to be given in divided daily doses, the amount in the unit dosage form is reduced accordingly. Such compositions for oral or parenteral administration can be prepared by standard pharmaceutical methods. For example, a suitable pharmaceutical or veterinary formulations for oral administration of the combination include tablets comprising the active ingredients and known pharmaceutical carriers and excipients such as starch, sugars, lubricants, certain types of clay and the like. Also included are suspensions or syrups, in which the active ingredients ordinarily constitute 10 to 60% by weight of the composition associated with a pharmaceutically acceptable suspending agent. Suitable suspending agents are described in "Remington's Pharmaceutical Sciences", J. E. Hoover, Ed., 15th ed., Mack Publishing Co., Easton, Penn., 1975. The amounts of the anxiolytic agent and β-AA preferably are proportioned so that the formulation provides the combination in unit dosage form.

For instance, a unit dosage form of cetamolol and diazepam can be proportioned to give a dosage form which, taken orally two to four times a day, would provide 0.03 to 0.28 mg/kg of body weight of diazepam and 0.14 to 1.1 mg/kg of body weight of cetamolol hydrochloride to the patient.

More explicitly exemplified, a suitable therapeutic composition for oral use can be prepared by mixing in a mechanical blender 2.0 grams of diazepam, 18.0 grams of cetamolol hydrochloride and 180 grams of lactose, each ingredient having been previously passed through a 20 mesh/cm sieve. The resulting mixture is then metered into capsules in amounts of 200 mg per capsule to provide 1000 capsules each containing 20 mg of the combination of therapeutic agent. Such tablets, when taken three times a day by a 70 kg patient, would provide 0.09 mg/kg of diazepam and 0.77 mg/kg of cetamolol hydrochloride, per day.

A further aspect of the present provides a pack or dispenser-device containing the two active agents separately and adapted for the concomitant administration of said active agents. Such packs and dispenser-devices may be constructed or devised in accordance with methods known in the art. Preferably, the pack or dispenser-device bears directions for the concomitant administration of a predetermined amount of the two active agents.

I claim:

1. A method for treating pathological states of anxiety, stress or aggressivity in a mammal, without eliciting sedative effects or altering motoricity, which comprises: administering to the mammal an effective amount of a combination of a β-adrenoceptor antagonist, which does not penetrate or penetrates poorly the brain, and is selected from the group consisting of cetamolol, atenolol, nifenalol, sotalol, acebutalol, nadolol, carteolol and timolol, and one quarter to one half of the normally effective dose of a benzodiazepine tranquilizer.

2. The method of claim 1 wherein the anxiolytic agent is diazepam employed at a daily dose ranging from 0.03 to 0.28 mg/kg of body weight per day.

3. The method of claim 1 wherein the β-adrenoceptor antagonist is cetamolol, atenolol, nifenalol, sotalol and timolol.

4. The method of claim 2 wherein cetamolol hydrochloride is employed at a daily dose ranging from 0.14 to 1.1 mg/kg of body weight.

5. The method of claim 2 wherein atenolol is employed at a daily dose ranging from 0.72–1.4 mg/kg of body weight.

6. A pharmaceutical composition in unit dosage form for treating pathological states of anxiety, stress or aggressivity comprising an effective therapeutic amount of a β-adrenoceptor antagonist, which does not penetrate or penetrates poorly the brain and is selected from the group consisting of cetamolol, "atenolol, nifenalol, sotalol, nadolol, carteolol and timolol; and one quarter to one half of the normally effective dose of a benzodiazepine tranquilizer; and a" subtherapeutical amount of a benzodiazepine tranquilizer; and a pharmaceutically acceptable carrier.

7. The pharmaceutical composition of claim 6 wherein the β-adrenoceptor antagonist is cetamolol.

8. The pharmaceutical composition of claim 7 wherein the anxiolytic agent is diazepam present in an amount which would provide 0.03 to 0.28 mg of diazepam per kg of body weight to a 70 kg patient taking the pharmaceutical composition two to four times a day.

* * * * *